(12) United States Patent
Ishigami

(10) Patent No.: US 8,480,572 B2
(45) Date of Patent: Jul. 9, 2013

(54) ADAPTER-TYPE ENDOSCOPE AND METHOD OF CLOSELY CONTACTING ELECTRICAL CONNECTION PORTION MAIN BODY OF ADAPTER-TYPE ENDOSCOPE AND ELECTRODE, AND ADAPTER MAIN BODY AND DISTAL END PORTION MAIN BODY

(75) Inventor: Takakazu Ishigami, Tama (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 12/704,639

(22) Filed: Feb. 12, 2010

(65) Prior Publication Data

US 2010/0217084 A1    Aug. 26, 2010

(30) Foreign Application Priority Data

Feb. 25, 2009    (JP) ................. 2009-042892

(51) Int. Cl.
  *A61B 1/06*    (2006.01)
  *A61B 1/04*    (2006.01)
(52) U.S. Cl.
  USPC ........................... 600/179; 600/160; 600/110
(58) Field of Classification Search
  USPC ............... 600/127, 129, 169, 172, 173, 175, 600/160, 110
  See application file for complete search history.

(56) References Cited

U.S. PATENT DOCUMENTS

| | | | | |
|---|---|---|---|---|
| 4,301,790 | A * | 11/1981 | Bol et al. ................... | 600/109 |
| 5,531,664 | A * | 7/1996 | Adachi et al. ............ | 600/149 |
| 6,036,636 | A * | 3/2000 | Motoki et al. ............ | 600/146 |
| 6,371,907 | B1 * | 4/2002 | Hasegawa et al. ........ | 600/146 |
| 6,796,939 | B1 * | 9/2004 | Hirata et al. .............. | 600/179 |
| 7,413,543 | B2 * | 8/2008 | Banik et al. .............. | 600/129 |
| 7,422,356 | B2 * | 9/2008 | Hama et al. .............. | 362/574 |
| 7,549,958 | B2 * | 6/2009 | Hirata ....................... | 600/179 |
| 7,914,448 | B2 * | 3/2011 | Bob et al. .................. | 600/175 |
| 8,308,637 | B2 * | 11/2012 | Ishigami et al. .......... | 600/177 |
| 2001/0056280 | A1 * | 12/2001 | Underwood et al. ...... | 606/41 |
| 2006/0183977 | A1 * | 8/2006 | Ishigami et al. .......... | 600/179 |
| 2007/0203397 | A1 * | 8/2007 | Kanzaki .................... | 600/175 |
| 2008/0300457 | A1 * | 12/2008 | Hosaka et al. ............ | 600/110 |

FOREIGN PATENT DOCUMENTS

| | | |
|---|---|---|
| JP | 2004-248835 | 9/2004 |
| JP | 2007-195798 | 8/2007 |
| JP | 2008-155016 | 7/2008 |

OTHER PUBLICATIONS

Office Action issued by the Japanese Patent Office on Apr. 30, 2013 in connection with corresponding Japanese Patent Application No. 2009-042892.

* cited by examiner

*Primary Examiner* — Philip R Smith
*Assistant Examiner* — William Chou
(74) *Attorney, Agent, or Firm* — Ostrolenk Faber LLP

(57) ABSTRACT

An adapter-type endoscope includes a distal end adapter and an insertion portion. The distal end adapter includes a light-emitting device substrate and an adapter-side electrical connection portion. The insertion portion includes a distal end portion to which the distal end adapter is detachably mounted, and has an insertion portion-side electrical connection portion connected to an adapter-side electrical connection portion, and a dual-purpose wire for power supply and heat release serving as both a heat releasing wire and a power source wire. The adapter-side electrical connection portion includes an electrical connection portion main body serving as both an electrical connection portion and a heat conducting portion and whose distal end surface closely contacts the light-emitting device substrate. The insertion portion-side electrical connection portion includes an electrode serving as both an electrical connection portion and a heat conducting portion and having a close-contact surface closely contacting the electrical connection portion main body.

11 Claims, 10 Drawing Sheets

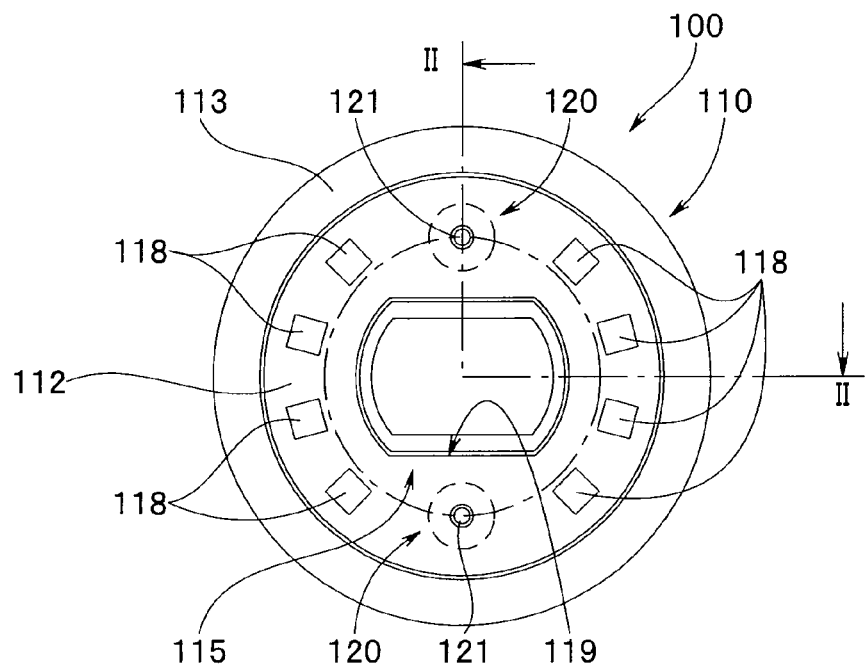
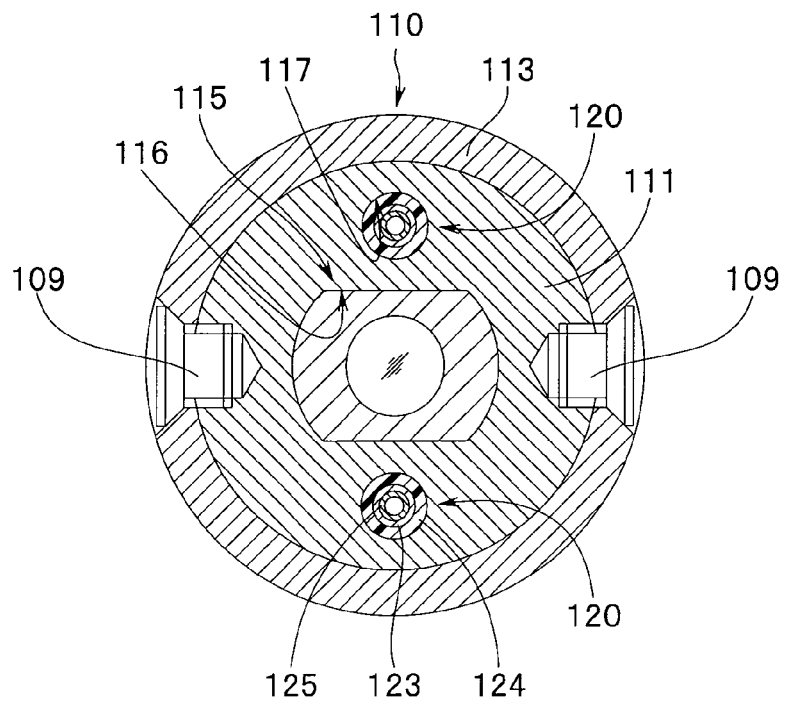

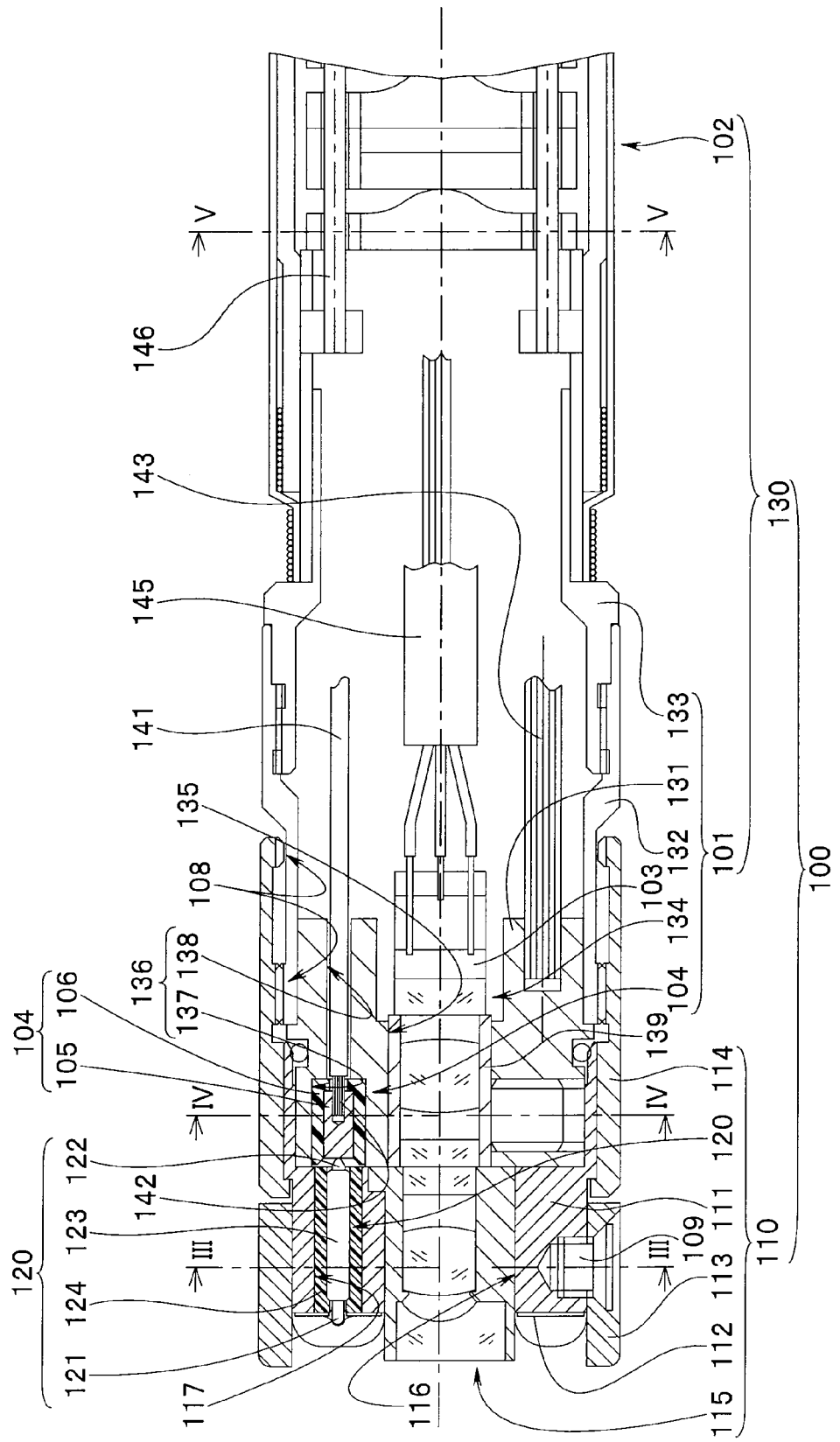

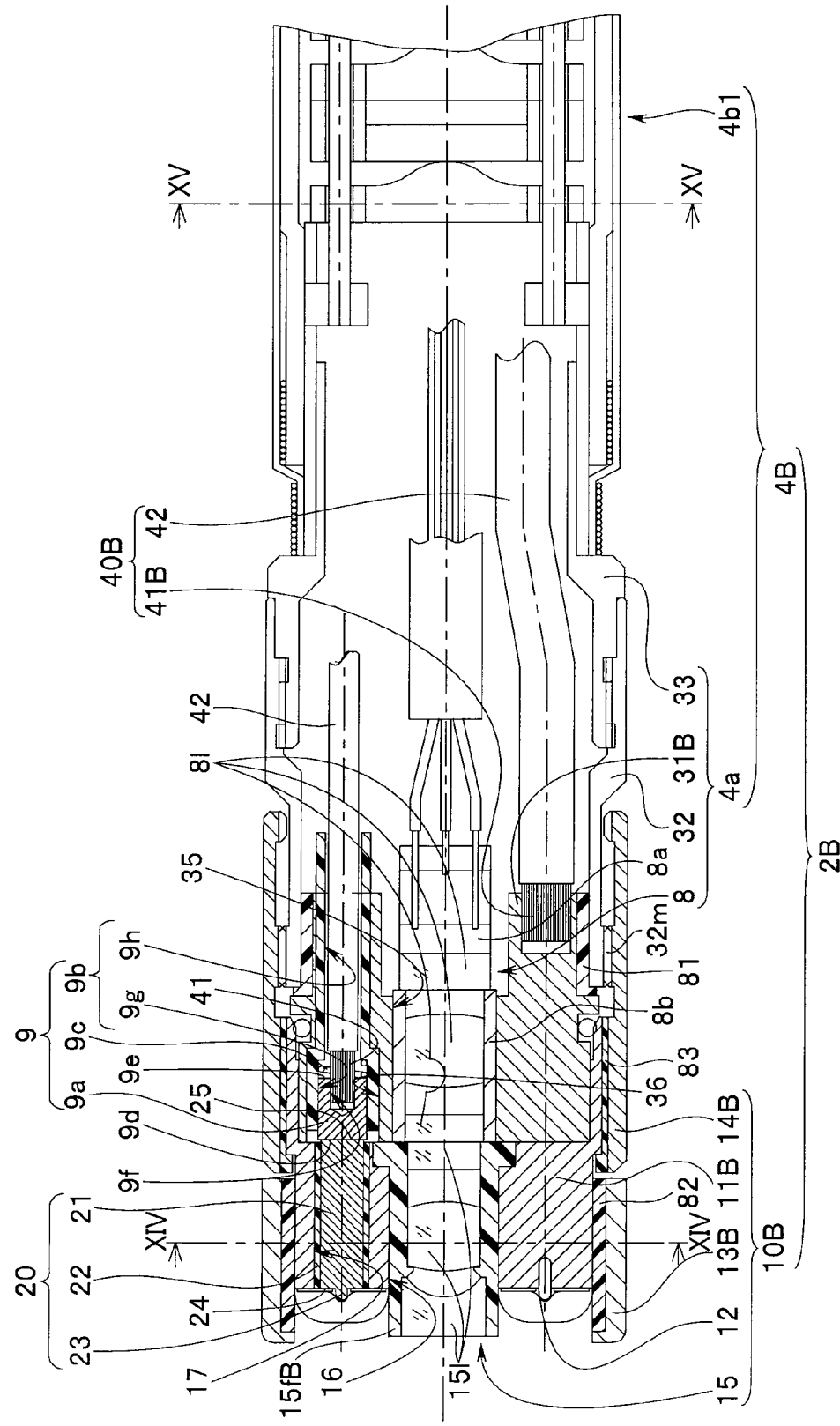

ADAPTER-TYPE ENDOSCOPE AND METHOD OF CLOSELY CONTACTING ELECTRICAL CONNECTION PORTION MAIN BODY OF ADAPTER-TYPE ENDOSCOPE AND ELECTRODE, AND ADAPTER MAIN BODY AND DISTAL END PORTION MAIN BODY

This Application claims benefit of Japanese Application No. 2009-042892 filed in Japan on Feb. 25, 2009, the contents of which are incorporated by this reference.

BACKGROUND OF THE INVENTION

1. Field of the Invention

The present invention relates to an adapter-type endoscope that includes light-emitting devices in a distal end adapter as an illumination optical system of an endoscope, in which the distal end adapter can be exchangeably mounted to an insertion portion.

2. Description of the Related Art

Since the examination target of an endoscope is the inside of a living body or a pipe at a plant or the like, an endoscope requires a light source that illuminates the examination target. In a common endoscope apparatus, a light source device is prepared as an external apparatus of the endoscope. The illumination light emitted by the light source device is supplied to a light guide provided in the endoscope.

In recent years, endoscopes are also being practically applied in which LED illuminations that are light-emitting devices are provided at a distal end portion of an insertion portion. Such endoscopes are configured to illuminate an examination target with the light emitted from the LED illuminations. In an endoscope that includes LED illuminations, an electric wire that supplies power is arranged inside the insertion portion instead of a light guide. Hence, it is possible to realize an endoscope with high functionality and a simple configuration that has an insertion portion with a small diameter.

However, in an endoscope that includes LED illuminations, there is the risk of problems occurring due to heat emitted from the LED illuminations. These problems include a decrease in the illumination light amount or an increase in the temperature of an image pickup device leading to the generation of image noise.

For example, Japanese Patent Application Laid-Open Publication No. 2004-248835 (hereunder, referred to as Document 1) discloses an endoscope that prevents problems including a decrease in the illumination light amount or generation of image noise due to heat emitted by LED illuminations installed at a distal end portion of an insertion portion, and can perform favorable observation over a long time.

This endoscope includes a bundled wire member as a heat releasing member. One end of the bundled wire member is installed in the vicinity of the LED illuminations. The other end of the bundled wire member is installed in a flexible tube portion included in the insertion portion. According to this configuration, since heat emitted from LED illuminations provided in the distal end portion is released by the bundled wire member, it is possible to prevent the LED illuminations from becoming a high temperature and prevent heat of the LED illuminations being conducted to the image pickup device.

In recent years, an adapter-type endoscope is also being practically applied in which a distal end adapter that includes light-emitting devices as an illumination optical system is exchangeably mounted to an insertion portion of an endoscope. With this adapter-type endoscope also, it is necessary to release heat generated from LED illuminations and the like provided in the distal end adapter. Therefore, the adapter-type endoscope is provided with a bundled wire member that is substantially the same as in the aforementioned Document 1 as shown in FIG. 1 to FIG. 5. Heat emitted by the LED illuminations is released by the bundled wire member to thereby prevent a problem whereby the amount of illumination light decreases or image noise is generated.

A configuration example of the conventional adapter-type endoscope will now be described referring to FIG. 1 to FIG. 5. FIG. 1 is a front view of an adapter-type endoscope. FIG. 2 is a cross section in the longitudinal direction of the adapter-type endoscope along a line II-II in FIG. 1. FIG. 3 is a cross section along a line III-III in FIG. 2. FIG. 4 is a cross section along a line IV-IV in FIG. 2. FIG. 5 is a cross section along a line V-V in FIG. 2.

As shown in FIG. 2, an adapter-type endoscope 100 includes a distal end adapter 110 and an insertion portion 130 to which the distal end adapter 110 is detachably mounted.

As shown in FIG. 1, FIG. 2, and FIG. 3, the distal end adapter 110 includes an adapter main body 111, an LED substrate 112, a cylinder 113, a detachable ring 114, an observation optical system 115, and a pair of adapter-side electrical connection portions 120 and the like. LED illuminations 118 are mounted on the LED substrate 112.

The adapter main body 111 is a receiving member for the LED illuminations 118, and conducts heat generated at the LED illuminations 118. As shown in FIG. 2 and FIG. 3, the adapter main body 111 includes a first through hole 116 and a pair of second through holes 117. The observation optical system 115 is installed in the first through hole 116. The adapter-side electrical connection portions 120 are installed in the second through holes 117, respectively.

The cylinder 113 is integrally fixed to the adapter main body 111 by, for example, two fixing screws 109 as shown in FIG. 3.

As shown in FIG. 2, the detachable ring 114 is rotatably mounted with respect to the adapter main body 111. The ring 114 includes a female screw portion 108 on the inner peripheral surface thereof.

The LED substrate 112 has, for example, a disk shape as shown in FIG. 1. The substrate 112 includes a conductive pattern (not shown) on one surface side. A plurality of LED illuminations 118 are mounted at predetermined positions on the conductive pattern. Further, contact pins 121 of the adapter-side electrical connection portions 120 are connected to the conductive pattern of the LED substrate 112. A central through-hole 119 for installing the observation optical system 115 is formed in the LED substrate 112.

As shown in FIG. 2, the adapter-side electrical connection portion 120 mainly includes the contact pins 121, an abutting pin 122, a case body 123, and an insulation cylinder 124. As shown in FIG. 3, a coil spring 125 is arranged inside the case body 123. The abutting pin 122 is configured to advance or retract with respect to the case body 123.

The contact pins 121, abutting pin 122, case body 123, and coil spring 125 are formed with a conductive member of aluminum, brass, iron, or the like.

As shown in FIG. 2, the insertion portion 130 includes a distal end portion 101, a bending portion 102, and a flexible tube portion (unshown) that are sequentially connected. For example, the distal end portion 101 includes a distal end portion main body 131, a first outer sheath portion 132, a second outer sheath portion 133, an image pickup optical system 134 having an image pickup device 103 and the like, and an endoscope-side electrical connection portion 104.

As shown in FIG. 2 and FIG. 4, the endoscope-side electrical connection portion 104 includes a cylindrically shaped electrode 105 and a tubular insulating portion 106. The distal end portion main body 131 is a receiving member that abuts against the adapter main body 111 and conducts heat that has been conducted to the adapter main body 111. A through hole 135 and a pair of stepped through-holes 136 are formed in the distal end portion main body 131. The image pickup optical system 134 is installed in the through hole 135. As shown in FIG. 4, a distal end surface of a fixing screw 107 is pressed against an image pickup frame 139 included in the image pickup optical system 134 to thereby integrally fix the image pickup optical system 134 to the distal end portion main body 131.

As shown in FIG. 2, the stepped through-hole 136 includes a large-diameter hole 137 and a small-diameter hole 138. The endoscope-side electrical connection portion 104 is fixedly arranged in the large-diameter hole 137. A power source wire 141 for supplying power to the LED illuminations 118 is inserted through the small-diameter hole 138.

The configuration is such that, by means of an urging force of the coil spring 125, the abutting pin 122 of the adapter-side electrical connection portion 120 abuts against a surface of the electrode 105 of the endoscope-side electrical connection portion 104 that is fixedly arranged in the large-diameter hole 137. A hole is formed in the other end of the electrode 105. A conducting wire 142 of the power source wire 141 is electrically connected inside the hole. The conducting wire 142 passes through the through hole of the insulating portion 106 to be installed inside the hole of the electrode 105.

One end of a bundled wire member 143 for releasing heat is connected to the distal end portion main body 131. As shown in FIG. 5, for example, four bundled wire members 143 extend from the distal end portion main body 131.

As shown in FIG. 2 and FIG. 5, the power source wires 141 and the bundled wire members 143 are inserted through the inside of the bending portion 102 from the distal end portion main body 131 and extend in the direction of the flexible tube portion. Reference numeral 145 denotes a signal wire that extends from the image pickup optical system 134. Reference numerals 146 denote bending wires.

According to the adapter-type endoscope 100 configured as described above, heat generated at the LED illuminations 118 is conducted to the adapter main body 111 via the LED substrate 112. The heat conducted to the adapter main body 111 is subsequently conducted to the distal end portion main body 131 of the insertion portion 130, and thereafter conducted to the bundled wire members 143 extending from the distal end portion main body 131. The heat is released inside the insertion portion 130 and the like to thereby prevent occurrence of a problem due to a rise in temperature.

However, with respect to adapter-type endoscopes also, users desire that the insertion portion is provided with a small diameter. In the case of an adapter-type endoscope, when the diameter of the insertion portion is made smaller, the outer dimensions of the adapter main body that conducts heat and the outer dimensions of the distal end portion main body also become smaller. Hence it is difficult to secure space for providing bundled wire members.

SUMMARY OF THE INVENTION

An adapter-type endoscope of the present invention includes:

a distal end adapter including a light-emitting device substrate on which a light-emitting device is mounted, and an adapter-side electrical connection portion that is electrically connected to the light-emitting device substrate; and an insertion portion including an insertion portion-side electrical connection portion which includes a distal end portion to which the distal end adapter can be detachably mounted and which is electrically connected to the adapter-side electrical connection portion when the distal end adapter is mounted to the distal end portion, and a dual-purpose wire for power supply and heat release whose distal end portion is fixed to the insertion portion-side electrical connection portion and which serves as both a heat releasing wire that releases heat and a power source wire that supplies power;

wherein the adapter-side electrical connection portion is formed with a solid conductive member that is arranged inside a through hole formed in an adapter main body constituting the distal end adapter, and includes an electrical connection portion main body that serves as both an electrical connection portion and a heat conducting portion whose distal end surface closely contacts a rear end surface of the light-emitting device substrate; and the insertion portion-side electrical connection portion is formed with a solid conductive member arranged inside a through hole formed in a distal end portion main body constituting the distal end portion, and includes an electrode that serves as both an electrical connection portion and a heat conducting portion and has a close-contact surface that closely contacts a rear end surface of the electrical connection portion main body.

The above and other objects, features and advantages of the invention will become more clearly understood from the following description referring to the accompanying drawings.

BRIEF DESCRIPTION OF THE DRAWINGS

FIG. 1 to FIG. 5 are views that describe a configuration example of a conventional adapter-type endoscope, in which:
FIG. 1 is a front view of an adapter-type endoscope;
FIG. 2 is a cross section in the longitudinal direction of the adapter-type endoscope along a line II-II in FIG. 1;
FIG. 3 is a cross section along a line III-III in FIG. 2;
FIG. 4 is a cross section along a line IV-IV in FIG. 2; and
FIG. 5 is a cross section along a line V-V in FIG. 2;
FIG. 6 to FIG. 10 relate to a first embodiment of the present invention, in which:
FIG. 6 is a view that describes a configuration of an adapter-type endoscope apparatus;
FIG. 7 is a front view of an adapter-type endoscope;
FIG. 8 is a cross section along a line VIII-VIII in FIG. 7;
FIG. 9 is a cross section along a line IX-IX in FIG. 8; and
FIG. 10 is a cross section along a line X-X in FIG. 8;
FIG. 11 and FIG. 12 are views that describe another configuration example of an insertion portion-side electrical connection portion, in which:
FIG. 11 is a cross section in the longitudinal direction of an adapter-type endoscope; and
FIG. 12 is a cross section along a line XII-XII in FIG. 11;
FIG. 13 to FIG. 15 relate to a second embodiment of the present invention, in which:
FIG. 13 is a cross section in the longitudinal direction of an adapter-type endoscope;
FIG. 14 is a cross section along a line XIV-XIV in FIG. 13; and
FIG. 15 is a cross section along a line XV-XV in FIG. 13.

DETAILED DESCRIPTION OF THE PREFERRED EMBODIMENTS

Hereunder, embodiments of the present invention are described with reference to the drawings.

A first embodiment of the present invention will be described with reference to FIG. 6 to FIG. 10.

Figure 4:
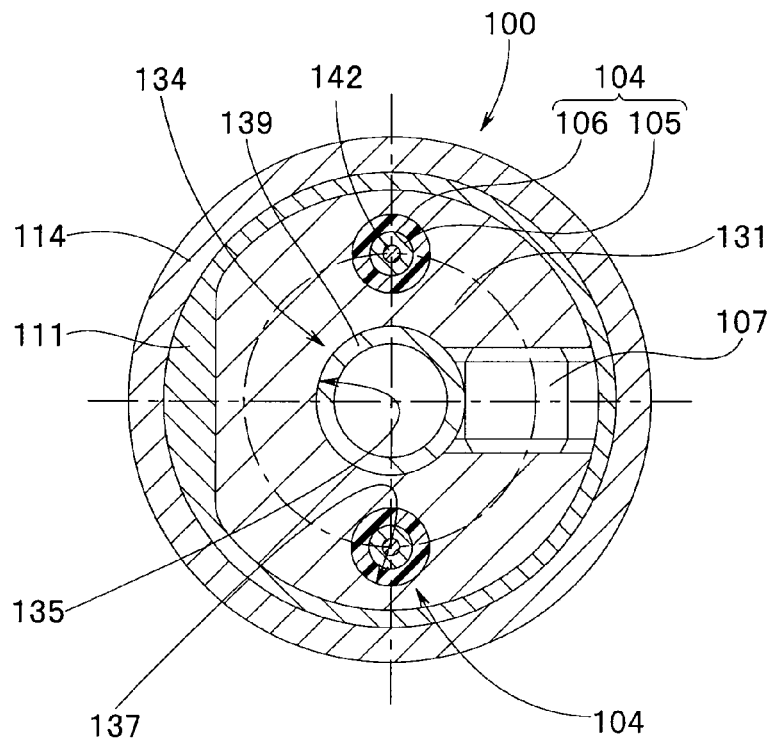
Figure 5:
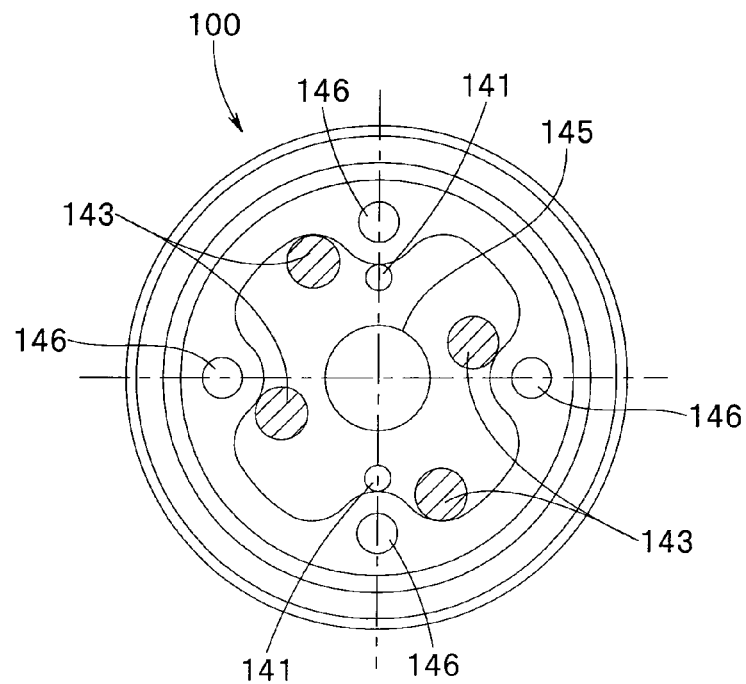
Figure 6:
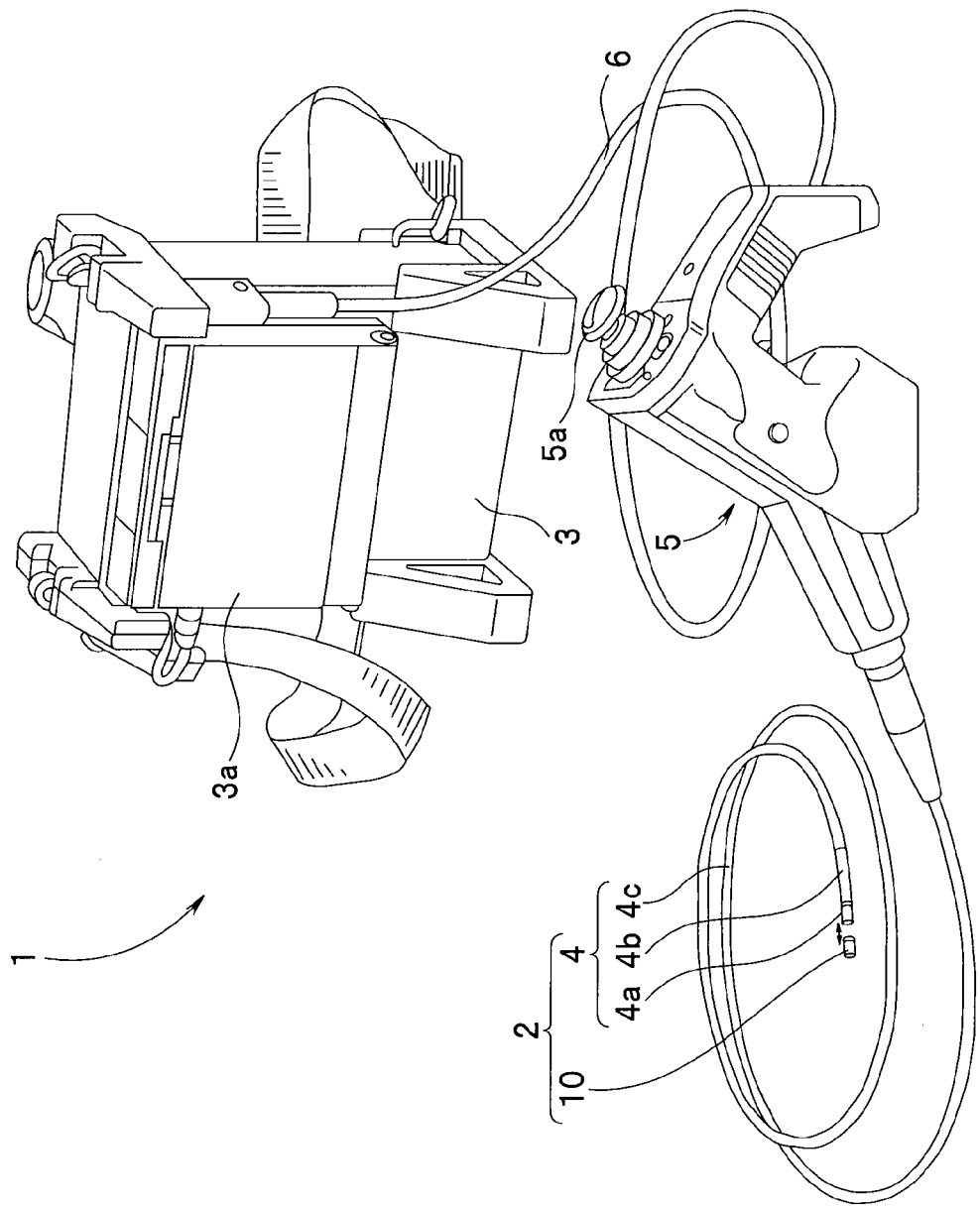

As shown in FIG. 6, an adapter-type endoscope apparatus 1 includes an adapter-type endoscope 2 and an apparatus main body 3 that is an external apparatus connected to the adapter-type endoscope 2 as main portions. Reference numeral 10 denotes a distal end adapter. The distal end adapter 10 of the present embodiment is configured with a smaller diameter (see FIG. 7) than the distal end adapter 110 shown in FIG. 1. An insertion portion 4 also has a smaller diameter than the insertion portion 130 shown in FIG. 2 (see FIG. 10).

The adapter-type endoscope 2 includes the distal end adapter 10, the insertion portion 4, an operation apparatus 5, and a universal cord 6 as main portions.

The insertion portion 4 is elongated and flexible. The insertion portion 4 includes, in order from the distal end side, a distal end portion 4a, a bending portion 4b, and a flexible tube portion 4c. The distal end portion 4a is rigid, and the distal end adapter 10 is detachably mounted thereto. The bending portion 4b includes a plurality of bending pieces that are sequentially connected, and is configured so as to bend, for example, in the vertical and horizontal directions. The flexible tube portion 4c is formed to be flexible.

The operation apparatus 5 is arranged at a rear end side of the flexible tube portion 4c included in the insertion portion 4. The operation apparatus 5 has a bending operation lever 5a. The bending operation lever 5a is provided in an upright condition on a predetermined surface of the operation apparatus 5, and is capable of a tilt operation. When the bending operation lever 5a is, for example, tilted by an operator, only a wire corresponding to the tilt direction of the lever 5a among bending operation wires (see reference numeral 46 in FIG. 8) that are inserted through the inside of the insertion portion 4 is pulled or slackened, so that the bending portion 4b bends in correspondence with the tilt direction of the lever 5a.

The universal cord 6 extends from the operation apparatus 5 and is flexible.

The apparatus main body 3 is provided at an end portion of the universal cord 6 that extends from the operation apparatus 5. The apparatus main body 3 is, for example, formed in a box shape. A substrate on which a plurality of electrical components such as a CPU for image processing are fixed, or a battery unit (unshown) that supplies power to LED illuminations (see reference numerals 18 in FIG. 7) as light-emitting devices, described later, included in the distal end adapter 10 and the like are provided inside the apparatus main body 3. Reference numeral 3a denotes a monitor. An endoscope image that is picked up by an image pickup device (see reference numeral 8a in FIG. 8) included in the adapter-type endoscope 2 is displayed on a screen of the monitor 3a.

According to the present embodiment, the distal end adapter 10 is a monocular forward viewing type that includes a forward-viewing optical system that observes a distal end side (insertion direction side) in a longitudinal axial direction of the insertion portion 4. In this connection, the distal end adapter 10 is not limited to a monocular forward viewing type, and may be a binocular forward viewing type, or a monocular side viewing type or a binocular side viewing type that includes a side-viewing optical system or the like.

Figure 7:
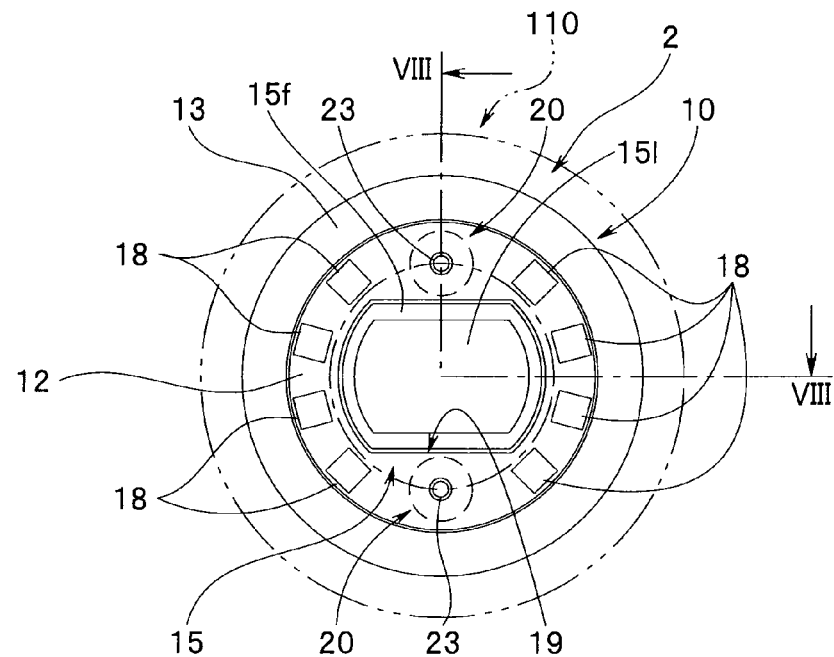
Figure 9:
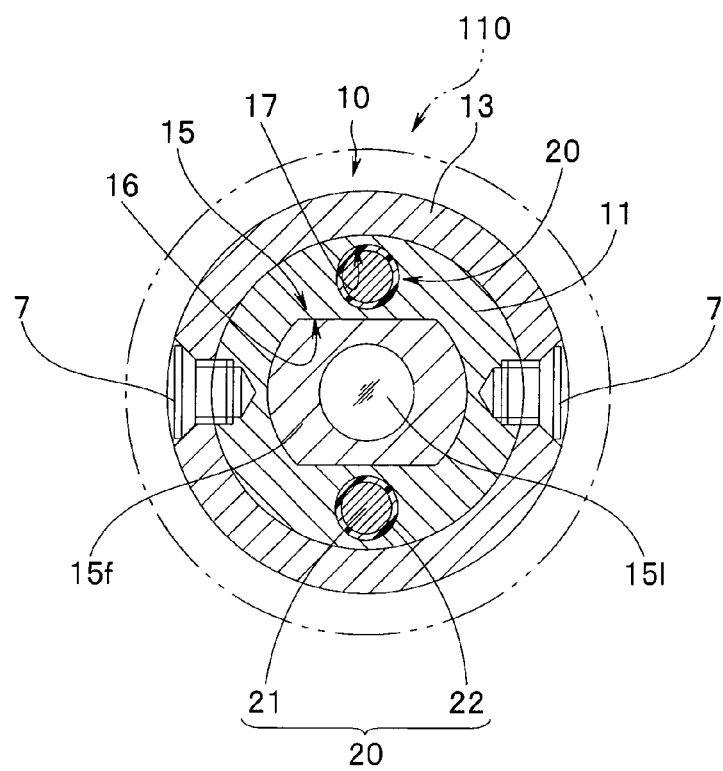
Figure 8:
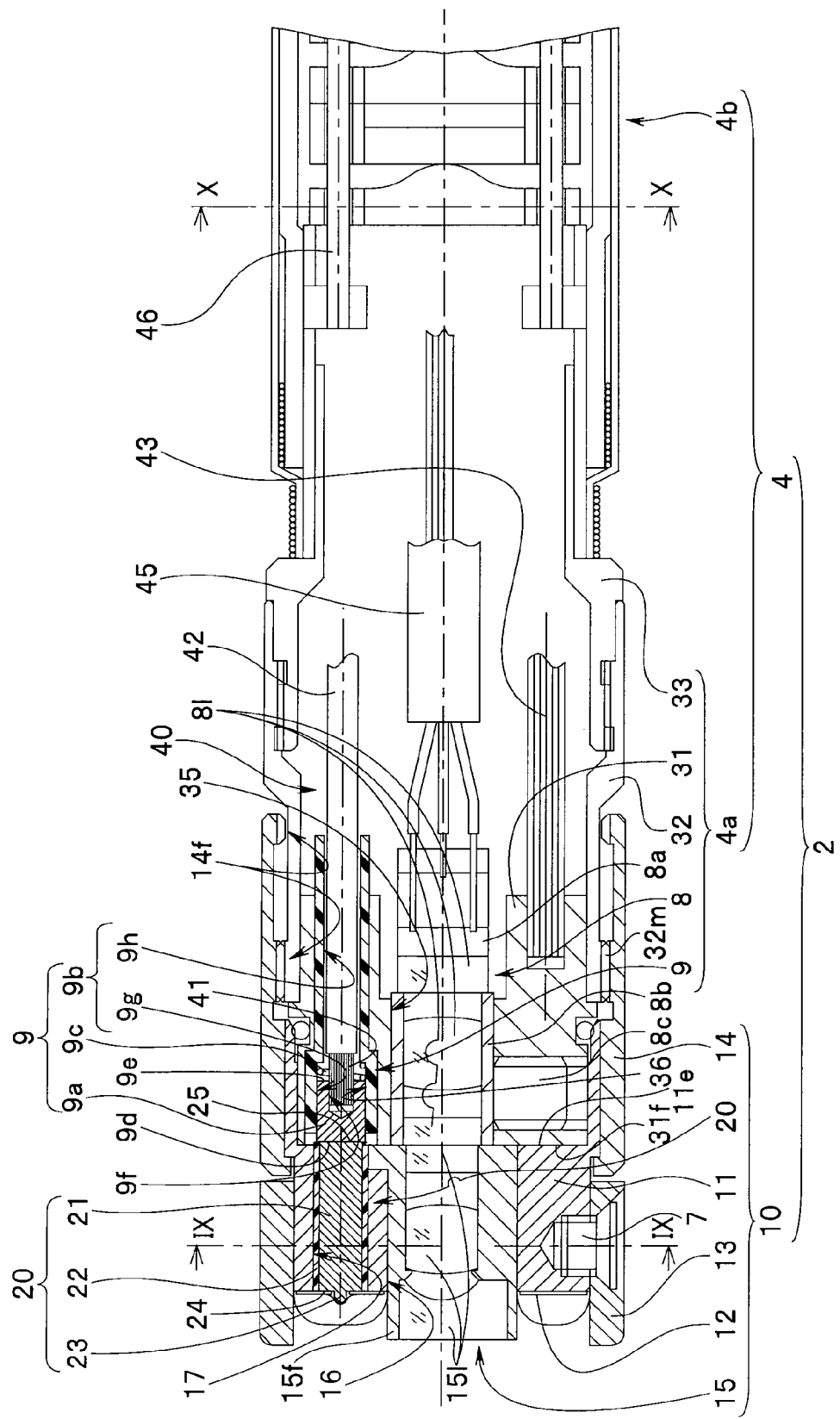

As shown in FIG. 7 to FIG. 9, the distal end adapter 10 includes an adapter main body 11, an LED substrate 12 as a light-emitting device substrate, a hood portion 13 that is a cylinder, a detachable ring 14, a forward-viewing optical system 15 as an observation optical system, and a pair of adapter-side electrical connection portions 20 and the like.

The hood portion 13 and the detachable ring 14 are outer sheath members of the adapter main body 11.

The adapter main body 11 is a receiving member to which heat of the LED illumination 18 is conveyed. The adapter main body 11 includes a heat conducting portion formed by, for example, brass, that is a conductive member having a high rate of thermal conductivity and is rigid. As shown in FIG. 8 and FIG. 9, an adapter-side first through hole 16 and a pair of adapter-side second through holes 17 are formed in the adapter main body 11. A plurality of optical lenses 15l constituting a forward-viewing optical system 15 are installed via a lens frame 15f in the adapter-side first through hole 16. An adapter-side electrical connection portion 20, described later, is installed in each of the adapter-side second through holes 17.

As shown in FIG. 7 and FIG. 9, the hood portion 13 is integrally fixed by, for example, two fixing screws 7 to the adapter main body 11. As shown in FIG. 8, the detachable ring 14 is rotatably attached to the adapter main body 11. The detachable ring 14 includes a female screw portion 14f on an inner peripheral surface thereof.

The LED substrate 12 is installed on a distal end surface side of the adapter main body 11. As shown in FIG. 7, the LED substrate 12 is, for example, disk shaped, and a conductive pattern (unshown) is provided on a distal end surface side that is one surface side. A plurality of LED illuminations 18 are mounted at predetermined positions on the conductive pattern. Contact portions 23 of the adapter-side electrical connection portion 20 are connected to predetermined positions of the conductive pattern. A central through-hole 19 for installing the lens frame 15f is formed in the LED substrate 12.

As shown in FIG. 8, the adapter-side electrical connection portion 20 includes an electrical connection portion main body 21 and an insulating tube 22. The electrical connection portion main body 21 is an adapter-side conductive portion that serves as both an electrical connection portion and a heat conducting portion. The insulating tube 22 covers the outer peripheral surface of the electrical connection portion main body 21, and prevents the electrical connection portion main body 21 from touching the adapter main body 11.

As shown in FIG. 8 and FIG. 9, the electrical connection portion main body 21 is a solid columnar shape. The electrical connection portion main body 21 is a cylindrical body made of brass, aluminum, iron, copper, silver or the like that is a conductive member that has a rate of thermal conductivity which is equal to that of the adapter main body 11.

The contact portions 23 that connect to the conductive pattern are provided at one end side of the electrical connection portion main body 21. The contact portions 23 are formed in a condition in which the contact portions 23 protrude from a distal end surface 24 that is configured with a flat surface. The distal end surface 24 is disposed in contact against the rear end surface of the LED substrate 12. The other end side of the electrical connection portion main body 21 is a rear end surface 25 that is configured with a flat surface. The distal end surface 24 and the rear end surface 25 are orthogonal with respect to a central axis of the electrical connection portion main body 21.

As shown in FIG. 8, the distal end portion 4a of the insertion portion 4 includes, for example, a distal end portion main body 31, a first outer sheath portion 32, a second outer sheath portion 33, an image pickup optical system 8 that includes an image pickup device 8a and the like, and an insertion portion-side electrical connection portion 9. The first outer sheath portion 32 includes a male screw portion 32m that meshes with the female screw portion 14f on the outer peripheral surface thereof. The first outer sheath portion 32 is an outer sheath member of the distal end portion main body 31.

The insertion portion-side electrical connection portion 9 includes a solid column-shaped electrode 9a, a tubular insulating portion 9b, and a coil spring 9c. A dual-purpose wire for power supply and heat release (hereunder, abbreviated to "dual-purpose wire") 40 is electrically connected to the insertion portion-side electrical connection portion 9.

Similarly to the electrical connection portion main body 21, the electrode 9a is an insertion portion-side conductive portion that serves as both an electrical connection portion and a heat conducting portion. The electrode 9a is a cylindrical body made of brass, aluminum, iron, copper, silver or the like. The external diameter dimensions of the electrode 9a are set to a smaller diameter than the external diameter dimensions of the adapter-side electrical connection portion 20. When the distal end adapter 10 is mounted to the distal end portion 4a, electrical contact of the electrode 9a with a member other than the electrical connection portion main body 21 included in the distal end adapter 10 is prevented.

The electrode 9a has a close-contact surface 9d and an abutting surface 9e that are configured with a flat surface at both ends thereof. The close-contact surface 9d is configured so as to closely contact the aforementioned rear end surface 25. A fixing hole 9f is formed on the abutting surface 9e side. The distal end portion of a bundled wire member 41 included in the dual-purpose wire 40 is installed inside the fixing hole 9f. The close-contact surface 9d and the abutting surface 9e are flat surfaces that are orthogonal with the central axis of the electrode 9a.

The insulating portion 9b is formed with, for example, a resin member that has slidability, and includes a large-diameter hole 9g and a small-diameter hole 9h. The large-diameter hole 9g also serves as a spring receiver. The electrode 9a and the coil spring 9c are installed inside the large-diameter hole 9g. The electrode 9a is installed so as to be slidable with respect to the large-diameter hole 9g. One end side of the coil spring 9c is installed on a stepped flat surface configured by the large-diameter hole 9g and the small-diameter hole 9h, and the other end side thereof contacts against the abutting surface 9e of the electrode 9a. The coil spring 9c has an urging force that pushes the electrode 9a to the outside from an opening in the large-diameter hole 9g.

The small-diameter hole 9h is a through hole that links the large-diameter hole 9g and the outside. The distal end portion of the dual-purpose wire 40 is inserted through the inside of the small-diameter hole 9h in a loosely fitted state.

The dual-purpose wire 40 includes a bundled wire member 41 and a sheath portion 42. The bundled wire member 41 of the dual-purpose wire 40 of the present embodiment is used both as a heat releasing wire and a power source wire. Therefore, in comparison to, for example, a lead wire that is a power source wire that is formed independently, the dual-purpose wire 40 is formed by taking into account the heat release characteristics thereof. More specifically, the bundled wire member 41 is formed by bundling a plurality of element wires that have a high rate of thermal conductivity such as copper wires, aluminum wires, or silver wires with a diameter of 0.1 mm or less, and is suitably made by taking into consideration both thermal capacity and workability as well as the diametrical dimensions of the insertion portion 4 and the like.

In the dual-purpose wire 40, the distal end side of the bundled wire member 41 is exposed with respect to the sheath portion 42. The distal end portion of the exposed bundled wire member 41 is installed inside the fixing hole 9f formed in the electrode 9a, and is integrally fixed to the electrode 9a by a solder or a thermally conductive adhesive.

The rear end portion of the bundled wire member 41 is inserted through the inside of the insertion portion 4, the inside of the operation apparatus 5, and the inside of the universal cord 6 and electrically connected to the battery unit.

The sheath portion 42 of the dual-purpose wire 40 is a flexible tube body formed with an insulation member, and covers the bundled wire member 41. The sheath portion 42 prevents the bundled wire member 41 from touching a metal member included within the insertion portion 4 or a metal member included within the adapter-type endoscope 2.

The distal end portion main body 31 is a receiving member to which heat conducted to the adapter main body 11 is further conducted. The distal end portion main body 31 is formed by a rigid conductive member that has a high rate of thermal conductivity such as, for example, brass, and constitutes a heat conducting portion. A distal end portion of a dedicated wire for releasing heat 43 that is a heat releasing member constituted by the bundled wire member 41 is fixed to the distal end portion main body 31. A rear end portion of the dedicated wire for releasing heat 43 is installed inside the flexible tube portion 4c.

An insertion portion-side first through hole 35 and a pair of insertion portion-side second through holes 36 are formed in the distal end portion main body 31. An image pickup frame 8b in which optical lenses 81 included in the image pickup optical system 8 are fixedly arranged is installed in the insertion portion-side first through hole 35. The image pickup frame 8b is integrally fixed to the distal end portion main body 31 by a fixing screw 8c.

An insulating portion 9b included in the insertion portion-side electrical connection portion 9 is installed in each of the insertion portion-side second through holes 36. The insulating portions 9b are integrally fixed by, for example, adhesion to the distal end portion main body 31. As a result, the electrode 9a is insulated with respect to the distal end portion main body 31.

In this connection, when the insertion portion-side electrical connection portion 9 is fixed in the insertion portion-side second through hole 36, the electrode 9a and the coil spring 9c are installed inside the large-diameter hole 9g of the insulating portion 9b. The dual-purpose wire 40 extends from the small-diameter hole 9h of the insulating portion 9b, and the bundled wire member 41 is fixed to the electrode 9a.

Figure 10:
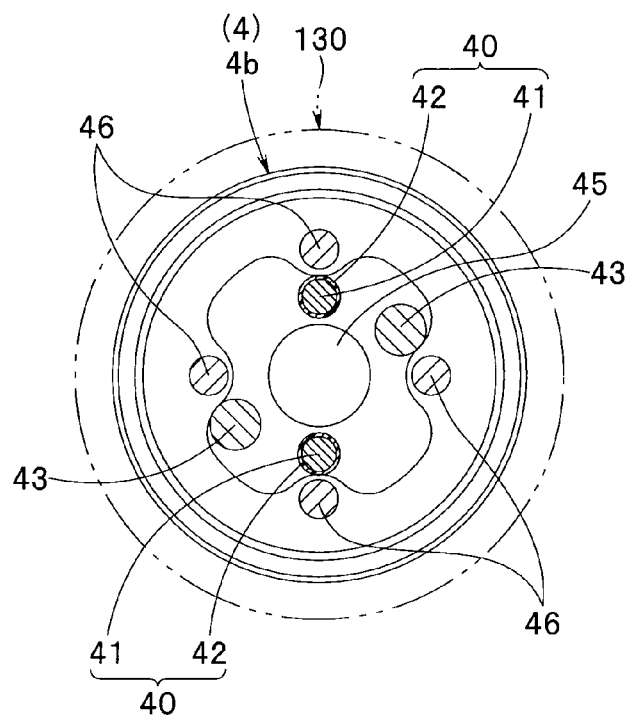

According to the present embodiment, the dual-purpose wires 40 and the dedicated wires for releasing heat 43 that extend in the direction of the flexible tube portion 4c from the distal end portion main body 31 are installed inside the bending portion 4b as shown in FIG. 10. Reference numeral 45 denotes a signal wire that extends from the image pickup optical system 8. Reference numerals 46 denote bending operation wires that are arranged so as to correspond to the vertical and horizontal directions.

Mounting of the distal end adapter 10 to the distal end portion 4a by the user will now be described.

When mounting the distal end adapter 10 to the distal end portion 4a, first, the user aligns the distal end adapter 10 and the distal end portion 4a so that the female screw portion 14f formed at the end portion of the detachable ring 14 and the male screw portion 32m formed in the first outer sheath portion 32 may screw together. Next, the user aligns the orientation of the adapter main body 11 and the distal end portion main body 31. Thereafter, the user rotates the detachable ring 14 to screw together the female screw portion 14f and the male screw portion 32m. Thereupon, the rear end surface 25 of the electrical connection portion main body 21 provided in the adapter main body 11 and the close-contact surface 9d of the electrode 9a provided in the distal end portion main body 31 contact against each other.

At this time, the user continues to rotate the detachable ring 14. Thereupon, the electrode 9a is moved in the direction of the stepped flat surface by the electrical connection portion main body 21 against the urging force of the coil spring 9c. Thus, as shown in FIG. 8, mounting of the distal end adapter 10 to the distal end portion 4a is completed. At this time, the state is one in which a rear end surface 11e of the adapter main body 11 and a distal end surface 31f of the distal end portion main body 31 abut in close contact with each other, and the rear end surface 25 of the electrical connection portion main body 21 and the close-contact surface 9d of the electrode 9a are retained in a closely contacting state by the urging force of the coil spring 9c.

The action of the adapter-type endoscope apparatus 1 configured as described above will now be described.

When starting observation, a surgeon turns on a power supply switch provided in the apparatus main body 3. Thereupon, power is supplied to the LED illuminations 18 via the bundled wire members 41 that also serve as power source wires of the dual-purpose wires 40, the electrode 9a, and the electrical connection portion main body 21. Thereupon, the LED illuminations 18 mounted on the LED substrate 12 enter a light emitting state, and the observation site is illuminated. As a result, an optical image of the observation site illuminated by the LED illuminations 18 passes through the forward-viewing optical system 15 and the optical lenses 15l and 8l of the image pickup optical system 8 to form and image on an image pickup surface of the image pickup device 8a, and an endoscope image is displayed on the screen of the monitor 3a.

During observation, heat is generated from the LED illuminations 18 when the LED illuminations 18 are lit. As observation continues, heat emitted from the LED illuminations 18 is first conducted to the LED substrate 12. In the present embodiment, heat that has been conducted to the LED substrate 12 is conducted to the electrical connection portion main body 21 whose distal end surface 24 is in close contact with the rear end surface of the LED substrate 12, and is also conducted to the adapter main body 11 installed at the rear end surface of the LED substrate 12.

Heat conducted to the adapter main body 11 is conducted to the distal end portion main body 31 whose distal end surface 31f contacts against the rear end surface 11e of the adapter main body 11. The heat conducted to the distal end portion main body 31 is conducted to the dedicated wires for releasing heat 43 whose distal end portion is fixed to the distal end portion main body 31. The heat that has been conducted to the dedicated wires for releasing heat 43 is conducted to the rear end portion side from the distal end portion side.

Meanwhile, the heat that has been conducted to the electrical connection portion main body 21 is conducted to the electrode 9a via the close-contact surface 9d that closely contacts the rear end surface 25 of the electrical connection portion main body 21. Thereafter, heat that has been conducted to the electrode 9a is conducted to the bundled wire members 41 that also serve as heat releasing wires of the dual-purpose wires 40 whose distal end portion is fixed to the electrode 9a. The heat conducted to the bundled wire members 41 is conducted from the distal end portion side to the rear end portion side.

By heat being conducted from the distal end portion side to the rear end portion side by means of the dedicated wires for releasing heat 43 and the dual-purpose wires 40, the LED illuminations 18 are prevented from reaching a high temperature.

Thus, the electrical connection portion main body included in the adapter-side electrical connection portion provided in the adapter main body and the electrode included in the insertion portion-side electrical connection portion provided in the distal end portion main body are formed with a solid conductive member that is a heat conducting member of the same level as the adapter main body and the distal end portion main body. As a result, the adapter-side electrical connection portion and the insertion portion-side electrical connection portion can be configured as similar heat conducting portions to the adapter main body and the distal end portion main body.

Consequently, by the adapter main body and the electrical connection portion main body provided in the adapter main body, as well as the distal end portion main body and the electrode provided in the distal end portion main body fulfilling functions as heat conducting portions, even when the adapter main body and the distal end portion main body are formed with a thin diameter, heat generated at the LED illuminations can be conducted efficiently to the dedicated wires for releasing heat and the bundled wire members constituting the dual-purpose wires.

Further, since heat generated at the LED illuminations and conducted to the LED substrate is conducted to the dedicated wires for releasing heat via the adapter main body and the distal end portion main body, and is then further conducted to the bundled wire members constituting the dual-purpose wires via the electrical connection portion main body of the adapter-side electrical connection portion and the electrode of the insertion portion-side electrical connection portion, a rise in the temperature of the LED illuminations can be prevented.

A configuration in which the adapter-side electrical connection portion and the insertion portion-side electrical connection portion are configured as heat conducting portions and in which heat generated at the LED illuminations and conducted to the LED substrate is released is not limited to the above described embodiment. For example, a configuration illustrated in FIG. 11 to FIG. 15 as described hereunder may be adopted.

Figure 12:
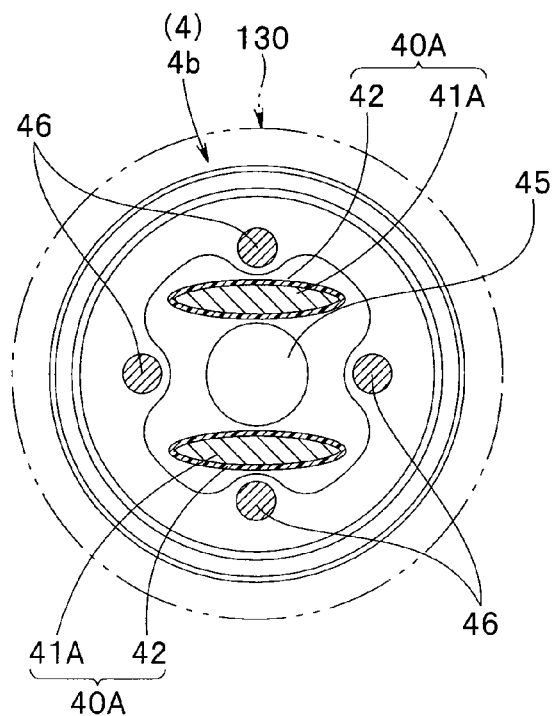
Figure 11:
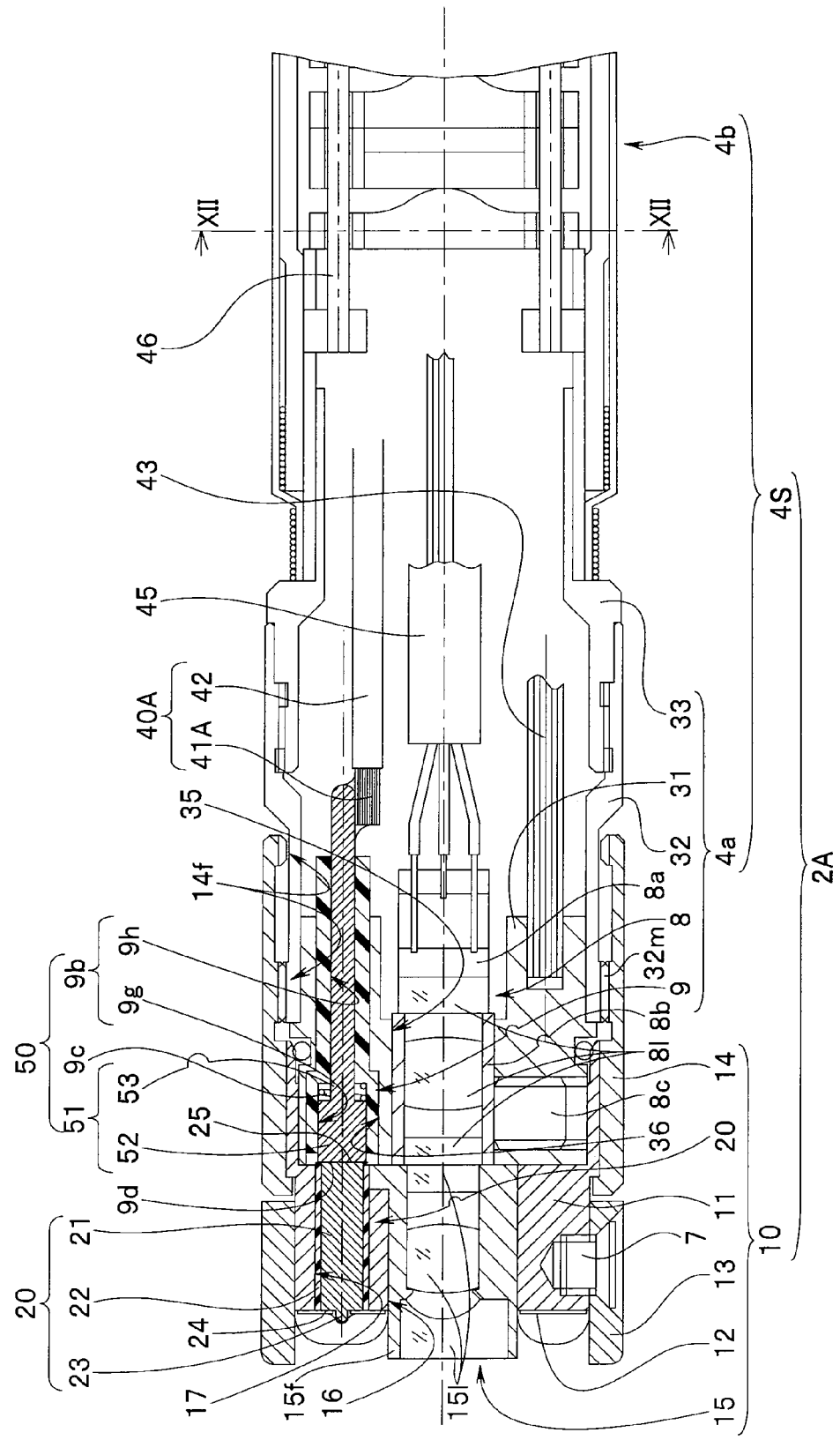

FIG. 11 and FIG. 12 are views that describe another configuration example of an insertion portion-side electrical connection portion. FIG. 11 is a cross section in the longitudinal direction of an adapter-type endoscope. FIG. 12 is a cross section along a line XII-XII in FIG. 11.

In an adapter-type endoscope 2A of the present embodiment, the diametrical dimensions of an insertion portion 4S are, for example, smaller than the diametrical dimensions of the insertion portion 4 of the adapter-type endoscope 2. Therefore, in the present embodiment, a configuration is adopted that releases heat conducted to the LED substrate 12 without providing the dedicated wire for releasing heat shown in the above described embodiment inside the insertion portion 4S, and only providing a dual-purpose wire 40A therein.

Consequently, the configuration of an electrode 51 of an insertion portion-side electrical connection portion 50 shown in FIG. 11 and the configuration of the dual-purpose wire 40A shown in FIG. 11 and FIG. 12 are different from the above described embodiment. The other components are the same as in the above described embodiment, and the same reference numerals are assigned to like members and a description of those members is omitted.

As shown in FIG. 11, the insertion portion-side electrical connection portion 50 of the present embodiment includes an electrode 51, a tubular insulating portion 9b, and a coil spring 9c. The dual-purpose wire 40A is electrically connected to the insertion portion-side electrical connection portion 50.

The electrode 51 has an elongated, stepped columnar shape that is solid, and serves as both an electrical connection portion and a heat conducting portion. Similarly to the electrode 9a, the electrode 51 is made of brass, aluminum, iron, copper, silver or the like. The electrode 51 of the present embodiment has a thick-diameter portion 52 and a thin-diameter portion 53.

The outer shape of the thick-diameter portion 52 of the electrode 51 is substantially the same as the shape of the electrode 9a. More specifically, to prevent the thick-diameter portion 52 from electrically contacting a member other than the electrical connection portion main body 21 as described above, the external diameter dimensions of the thick-diameter portion 52 are smaller than the external diameter dimensions of the adapter-side electrical connection portion 20. The electrode 51 has a close-contact surface 9d that is configured as a flat surface at the distal end of the thick-diameter portion 52.

The thin-diameter portion 53 of the electrode 51 is elongated. The length dimensions thereof are set so that the rear end portion thereof protrudes by a predetermined amount from the rear end surface of the insulating portion 9b. A distal end portion of a bundled wire member 41A, described later, is integrally fixed by, for example, a solder to the rear end portion of the thin-diameter portion 53 that protrudes from the rear end surface of the insulating portion 9b.

In the present embodiment, the thick-diameter portion 52 of the electrode 51 and the coil spring 9c are installed inside the large-diameter hole 9g of the insulating portion 9b. The thin-diameter portion 53 of the electrode 51 is inserted through the inside of the small-diameter hole 9h. The thick-diameter portion 52 of the electrode 51 is slidable with respect to the large-diameter hole 9g. The thin-diameter portion 53 is slidable with respect to the small-diameter hole 9h.

The coil spring 9c installed in the large-diameter hole 9g contacts against a stepped end surface formed by the thick-diameter portion 52 and the thin-diameter portion 53 of the electrode 51. The coil spring 9c has an urging force that pushes the thick-diameter portion 52 to the outside from the opening of the large-diameter hole 9g.

The dual-purpose wire 40A includes a bundled wire member 41A and a sheath portion 42. The bundled wire member 41A of the dual-purpose wire 40A of the present embodiment also serves as both a heat releasing wire and a power source wire. In the present embodiment, in order to increase the amount of heat that is released, the cross-sectional area of the bundled wire member 41A is made greater than the cross-sectional area of the bundled wire member 41. That is, as shown in FIG. 12, the cross-sectional shape of the bundled wire member 41A is a flat shape with a large cross-sectional area, and the bundled wire member 41A is housed inside the insertion portion 4S.

According to the present embodiment, similarly to the above described embodiment, heat that has been generated at the LED illuminations 18 and conducted to the LED substrate 12 is conducted to the electrical connection portion main body 21 whose distal end surface 24 is in close contact with the rear end surface of the LED substrate 12. The heat conducted to the electrical connection portion main body 21 is conducted to the electrode 51 included in the insertion portion-side electrical connection portion 50 via the close-contact surface 9d that is in close contact with the rear end surface 25 of the electrical connection portion main body 21. The heat conducted to the electrode 51 is conducted to the thin-diameter portion 53 from the thick-diameter portion 52, and conducted from the thick-diameter portion side of the thin-diameter portion 53 to the rear end portion side thereof. Thereafter, the heat that has been conducted to the rear end portion side of the thin-diameter portion 53 is conducted to the bundled wire members 41A of the dual-purpose wires 40A whose distal end portion is fixed to the thin-diameter portion 53, and is conducted from the distal end portion side thereof to the rear end portion side.

Thus, the electrode included in the insertion portion-side electrical connection portion is formed with a solid conductive member that has a rate of thermal conductivity equivalent to that of the adapter main body and the distal end portion main body. Bundled wire members are fixed to the rear end portion of the electrode. The bundled wire members are included in the dual-purpose wires and have a cross-sectional area that is set by taking into account an amount of heat to be released. Thus, heat that has been conducted to the LED substrate is conducted to the bundled wire members of the dual-purpose wires. It is therefore possible to prevent a problem caused by an increase in the temperature of the LED illuminations without providing a dedicated wire for releasing heat inside the insertion portion.

Figure 14:
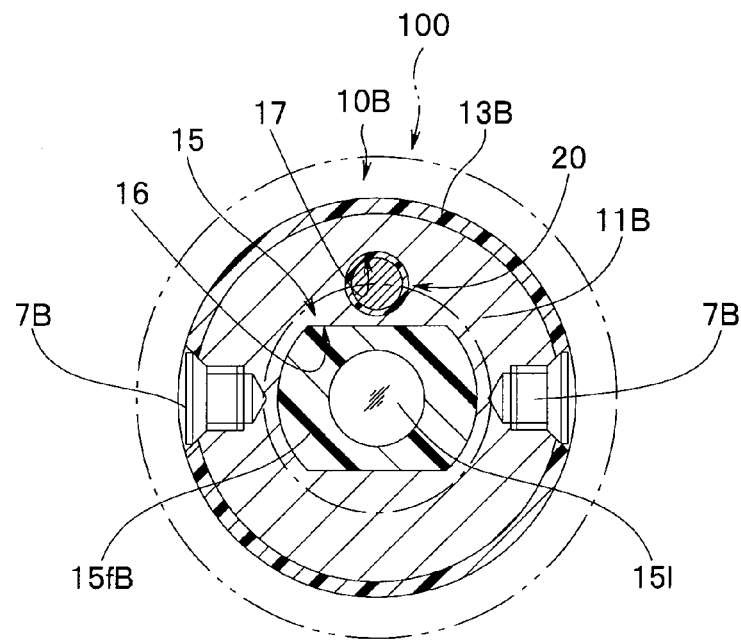
Figure 15:
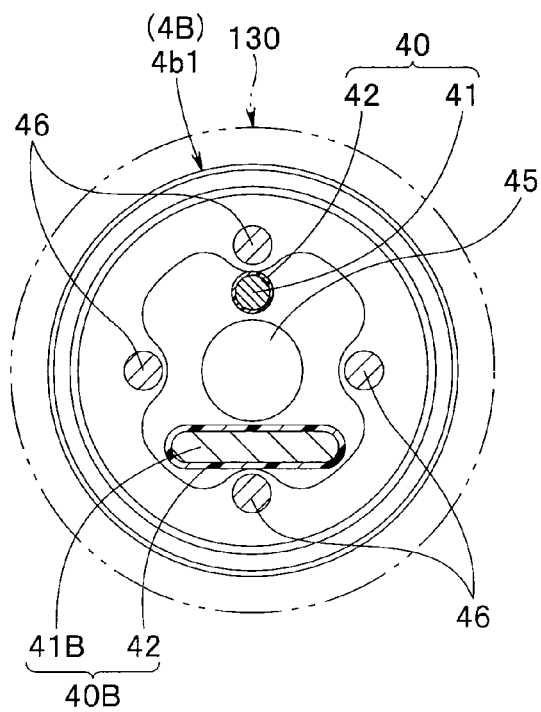

FIG. 13 to FIG. 15 relate to a second embodiment of the present invention. FIG. 13 is a cross section in the longitudinal direction of an adapter-type endoscope. FIG. 14 is a cross section along the line XIV-XIV in FIG. 13. FIG. 15 is a cross section along the line XV-XV in FIG. 13.

As shown in FIG. 13, in an adapter-type endoscope 2B of the present embodiment, one each of the dual-purpose wire 40 and a dual-purpose wire 40B are inserted through the inside of the insertion portion 4B. The distal end portion of the dual-purpose wire 40 is connected to the insertion portion-side electrical connection portion 9 constituting one of insertion portion electrical connection portions. The dual-purpose wire 40B is fixed to the rear end portion of the distal end portion main body 31B that volumetrically occupies the major part of the distal end portion 4a of the insertion portion 4B, and that constitutes the other insertion portion electrical connection portion.

By mounting the distal end adapter 10B to the distal end portion main body 31B of the insertion portion 4B, the insertion portion-side electrical connection portion 9 is electrically connected with the adapter-side electrical connection portion 20 constituting one of adapter electrical connection portions. The distal end portion main body 31B is electrically connected with an adapter main body 11B that volumetrically occupies the major part of the distal end adapter 10B constituting the other adapter electrical connection portion.

The dual-purpose wire 40B is substantially the same as the dual-purpose wire 40A. As shown in FIG. 13 and FIG. 15, the dual-purpose wire 40B includes a bundled wire member 41B and a sheath portion 42. The bundled wire member 41B serves as both a heat releasing wire and a power source wire. The cross-sectional area of the bundled wire member 41B is set in consideration of the amount of heat to be released.

In the present embodiment, since the adapter main body 11B itself constitutes the other adapter electrical connection portion, the cross-sectional area of the bundled wire member 41B can easily be set to be greater than the cross-sectional area of the bundled wire member 41A. By setting the cross-sectional area of the bundled wire member 41B as a large area, the amount of heat to be released can be increased. In this connection, within a bending portion 4b1, the bundled wire member 41B may be configured with a flat cross-sectional shape where necessary.

The distal end portion main body 31B is, for example, made of brass. As shown in FIG. 13, the distal end portion main body 31B includes the insertion portion-side first through hole 35 and a single insertion portion-side second through hole 36. The distal end portion of the bundled wire member 41B included in the dual-purpose wire 40B is fixed to the distal end portion main body 31B.

The adapter main body 11B to which the distal end portion main body 31B is electrically connected is, for example, made of brass. As shown in FIG. 14, the adapter main body 11B includes the adapter-side first through hole 16 and the adapter-side second through hole 17.

The distal end adapter 10B includes the adapter main body 11B, the LED substrate 12, a hood portion 13B, a detachable ring 14B, and the forward-viewing optical system 15 and the like.

In the present embodiment, reference numeral 81 denotes an insulating portion. The insulating portion 81 insulates the distal end portion main body 31B and the first outer sheath portion 32. A lens frame 15/B included in the forward-viewing optical system 15 is composed by an insulation member. An insulating portion 82 that contacts with the adapter main body 11B is provided on the inner peripheral surface of the hood portion 13B. Further, an insulating portion 83 that contacts with the adapter main body 11B is provided on the inner peripheral surface of the detachable ring 14B.

Reference numeral 7B denotes a fixing screw. The hood portion 13B and the adapter main body 11B are integrally fixed by the fixing screw 7B. The fixing screw 7B is composed by an insulation member, or an insulating portion is provided on the surface thereof According to this configuration, in a case where an outer sheath included in the adapter-type endoscope 2B touches a metal member such as an examination portion, an electric current can be prevented from flowing to the examination portion side. The insulating portion 81 is composed by an insulation member provided on the outer peripheral surface of the distal end portion main body 31B or by an insulating film. The insulating portion 82 is composed by an insulation member provided on the inner peripheral surface of the hood portion 13B or by an insulating film. The insulating portion 83 is composed by an insulation member provided on the inner peripheral surface of the detachable ring 14B or by an insulating film.

According to the present embodiment, heat generated at the LED illuminations 18 and conducted to the LED substrate 12 is conducted to the electrical connection portion main body 21 and the adapter main body 11B. The heat that has been conducted to the adapter main body 11B is conducted to the distal end portion main body 31B, and is further conducted to the bundled wire member 41B of the dual-purpose wire 40B whose distal end portion is fixed to the distal end portion main body 31B.

Similarly to the above described embodiment, heat conducted to the electrical connection portion main body 21 is conducted via the electrode 9a to the bundled wire member 41 of the dual-purpose wire 40.

Thus, one of the adapter electrical connection portions is constituted by an adapter-side conductive portion, and the other adapter electrical connection portion is constituted by the adapter main body that occupies the major part of the volume of the distal end adapter. Further, the insertion portion-side conductive portion to which the adapter-side conductive portion is electrically connected is configured as one of the insertion portion electrical connection portions, and the distal end portion main body that occupies the major part of the volume of the distal end portion of the insertion portion to which the adapter main body is electrically connected is configured as the other of the insertion portion electrical connection portions. Furthermore, the distal end portion of the bundled wire member included in the dual-purpose wire is fixed to the distal end portion main body and the insertion portion-side conductive portion.

Thus, heat that is generated at the LED illuminations and conducted to the LED substrate is conducted via the electrical connection portion main body and the electrode to the bundled wire member of the dual-purpose wire connected to the electrode and released, and is also conducted via the adapter main body and the distal end portion main body to the bundled wire member of the dual-purpose wire connected to the distal end portion main body. It is thereby possible to prevent a problem caused by an increase in the temperature of the LED illuminations.

The above embodiments describe configurations in which a dual-purpose wire is provided in an adapter-type endoscope. However, a configuration may also be adopted that provides an endoscope that enables replacement of LED illuminations when the lifetime of an LED illumination expires or an LED illumination stops working by disconnecting the distal end portion unit from a distal end portion assembly, and thereafter removing a dual-purpose wire and replacing the distal end portion unit.

Further, a configuration may be adopted in which a dual-purpose wire, for example, is provided in an observation apparatus or a repair apparatus or the like that includes an electrical device that generates heat at a distal end portion of an elongated insertion portion. It is thereby possible to conduct heat generated at the electrical device to the dual-purpose wire and release the heat without inserting and installing a heat releasing wire or the like inside an insertion portion of the observation apparatus or the repair apparatus.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An adapter-type endoscope apparatus, comprising:
a distal end adapter; and
an insertion portion,
wherein the distal end adapter comprises a light-emitting device substrate on which a light-emitting device is mounted; and
an adapter-side electrical connection portion which has a solid column shape and flat surfaces formed respectively at a distal end and a rear end, and is connected to the light-emitting device substrate with the flat surface at the distal end abutting in close surface contact with a rear end surface of the light-emitting device substrate, the flat surfaces being formed to be orthogonal with respect to a central axis of the adapter-side electrical connection portion and to have an area equivalent to a cross-sectional area of the adapter-side electrical connection portion, and the adapter-side electrical connection portion performing both a power supplying function and a heat releasing function,
wherein the insertion portion comprises a distal end portion to which the distal end adapter is detachably mounted; and
an insertion portion-side electrical connection portion which is provided separately from the adapter-side electrical connection portion, and has a solid column shape and a flat surface formed at a distal end to be orthogonal to a central axis of the insertion portion-side electrical connection portion and to have an area equivalent to a cross-sectional area of the insertion portion-side electrical connection portion, and wherein when the distal end adapter is mounted to the distal end portion, the flat surface at the distal end of the insertion portion-side electrical connection portion is brought into contact with the flat surface at the rear end of the adapter-side electrical connection portion to be in close surface contact with each other, an entire area of one of the flat surface at the distal end of the insertion portion-side electrical connection portion and the flat surface at the rear end of the adapter-side electrical connection portion being in close contact with the other of the flat surface at the distal end of the insertion portion-side electrical connection portion and the flat surface at the rear end of the adapter-side electrical connection portion, so that the insertion portion-side electrical connection portion performs a power supplying function of supplying power to the light-emitting device through the adapter-side electrical connection portion and a heat releasing function of releasing heat from the light-emitting device through the adapter-side electrical connection portion.

2. The adapter-type endoscope according to claim 1, wherein members comprising the electrical connection portion main body, the electrode, the adapter main body, and the distal end portion main body are conductive members that have equivalent rates of thermal conductivity.

3. The adapter-type endoscope according to claim 1, wherein:
the adapter-side electrical connection portion comprises an adapter main body comprising the distal end adapter, and an adapter-side conductive portion arranged inside a through hole formed in the adapter main body;
the insertion portion-side electrical connection portion comprises a distal end portion main body comprising a distal end portion of the insertion portion, and an insertion portion-side conductive portion arranged inside a through hole formed in the distal end portion main body; and
the dual-purpose wire for power supply and heat release is fixed to the distal end portion main body.

4. The adapter-type endoscope according to claim 3, wherein the adapter-side conductive portion and the insertion portion-side conductive portion comprise a solid conductive member made of brass, aluminum, iron, copper, silver or the like.

5. The adapter-type endoscope according to claim 3, wherein:
one each of two kinds of dual-purpose wires for power supply and heat release are inserted through an inside of the insertion portion;
a distal end portion of one of the dual-purpose wires for power supply and heat release is connected to the insertion portion-side electrical connection portion comprising one of insertion portion electrical connection portions; and a distal end portion of the other dual-purpose wire for power supply and heat release is fixed to a rear end portion of the distal end portion main body that volumetrically occupies a major part of a distal end portion of the insertion portion, which comprises another of the insertion portion electrical connection portions.

6. The adapter-type endoscope according to claim 5, wherein the distal end portion main body, an outer sheath member of the distal end portion main body, the adapter main body, and an outer sheath member of the adapter main body are conductive members; and
an insulating portion comprising an insulation member or an insulating film is provided between the distal end portion main body and the outer sheath member of the distal end portion main body, and between the adapter main body and the outer sheath member of the adapter main body.

7. The adapter-type endoscope according to claim 1, wherein the dual-purpose wire for power supply and heat release comprises a bundled wire member that serves as both a heat releasing wire and a power source wire that supplies power, and a sheath portion that is a flexible tube body formed with an insulation member that covers the bundled wire member; and
the bundled wire member is formed by bundling a plurality of element wires that have a high rate of thermal conductivity such as copper wires, aluminum wires, or silver wires with a diameter of 0.1 mm or less, and by taking into consideration diametrical dimensions of an insertion portion, thermal capacity, and workability.

8. The adapter-type endoscope according to claim 7, wherein a distal end side of the bundled wire member of the dual-purpose wire for power supply and heat release is exposed with respect to the sheath portion, and the distal end portion of the bundled wire member that is exposed is installed inside a fixing hole formed in a rear end surface of the electrode and is integrally fixed to the electrode by a solder or a thermally conductive adhesive.

9. The adapter-type endoscope according to claim 8, wherein, in order to increase an amount of heat that is released by the bundled wire member, a cross-sectional shape of the dual-purpose wire for power supply and heat release is a flat shape.

10. The adapter-type endoscope according to claim 1, wherein a distal end portion of a dedicated wire for releasing heat that is a heat releasing member comprising a bundled wire member is fixed to the distal end portion main body, and a rear end portion thereof is installed inside a flexible tube portion.

11. The adapter-type endoscope of claim 1, wherein the electrical connection portion main body of the adapter-side electrical connection portion is provided with a contact portion on a distal end surface of the electrical connection portion main body, the contact portion being configured to protrude from the distal end surface and connected to a conductive pattern provided on a distal end surface side of the light-emitting device substrate.

* * * * *